US012653385B2

(12) United States Patent
Dolan et al.

(10) Patent No.: US 12,653,385 B2
(45) Date of Patent: Jun. 16, 2026

(54) MEDICAL DEVICE HAVING ARTICULATION MEMBER AND METHODS OF USE

(71) Applicant: Boston Scientific Scimed, Inc., Maple Grove, MN (US)

(72) Inventors: Brent Dolan, Minneapolis, MN (US); Sean Powell, Holden, MA (US); Raymond David Gessler, III, Roberts, WI (US); Brian Paul Edison, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 663 days.

(21) Appl. No.: 17/992,975

(22) Filed: Nov. 23, 2022

(65) Prior Publication Data

US 2023/0165446 A1 Jun. 1, 2023

Related U.S. Application Data

(60) Provisional application No. 63/264,668, filed on Nov. 30, 2021.

(51) Int. Cl.
| *A61B 1/008* | (2006.01) |
| *A61B 1/005* | (2006.01) |
| *A61M 25/01* | (2006.01) |

(52) U.S. Cl.
CPC ............ *A61B 1/008* (2013.01); *A61B 1/0057* (2013.01); *A61B 1/0052* (2013.01); *A61B 1/0055* (2013.01); *A61M 25/0138* (2013.01)

(58) Field of Classification Search
CPC ..... A61B 1/008; A61B 1/0057; A61B 1/0052; A61B 1/0055; A61M 25/0138
See application file for complete search history.

(56) References Cited

U.S. PATENT DOCUMENTS

| 10,321,804 B2 | 6/2019 | Jacobsen et al. | |
| 2010/0048999 A1* | 2/2010 | Boulais ................ | A61B 1/0008 |
| | | | 600/141 |

(Continued)

FOREIGN PATENT DOCUMENTS

JP 2010259479 A 11/2010

OTHER PUBLICATIONS

International Search Report and Written Opinion in International Application No. PCT/US2022/050822, mailed Mar. 15, 2023 (12 pages).

*Primary Examiner* — Michael J Carey
*Assistant Examiner* — Olivia Grace Starkey
(74) *Attorney, Agent, or Firm* — Bookoff McAndrews, PLLC

(57) ABSTRACT

A medical device including a handle, a shaft extending from the handle, first and second articulation wires coupled to the handle, and an articulation member at a distal end of the shaft, wherein the articulation member includes a central longitudinal axis within a first bending plane. The first and second articulation wires lie within the first bending plane, the articulation member includes a plurality of links arranged about the central longitudinal axis, a first link of the plurality of links is attached to an adjacent, second link of the plurality of links via a first pair of hinges, and a first hinge from the first pair of hinges is arranged on a first side the first bending plane, and a second hinge from the first pair of hinges is located on a second side of the bending plane, opposite the first side.

16 Claims, 9 Drawing Sheets

(56)            References Cited

U.S. PATENT DOCUMENTS

2012/0165608 A1*  6/2012  Banik ................. A61B 1/00071
                                                       600/141
2016/0029878 A1*  2/2016  Yamazaki ............ A61B 1/0057
                                                       600/149
2017/0150879 A1*  6/2017  Matsuura .......... A61M 25/0147
2019/0099061 A1*  4/2019  Isobe ................... A61B 1/0055

* cited by examiner

MEDICAL DEVICE HAVING ARTICULATION MEMBER AND METHODS OF USE

CROSS-REFERENCE TO RELATED APPLICATIONS

This application claims the benefit of priority from U.S. Provisional Application No. 63/264,668, filed on Nov. 30, 2021, which is incorporated by reference herein in its entirety.

TECHNICAL FIELD

The disclosure relates generally to medical devices and related methods of use. For example, the disclosure relates to medical tools and methods related to accessing target sites using scopes and performing medical procedures at the target sites.

BACKGROUND

In certain medical procedures, it may be necessary to articulate a portion of a medical device, such as a scope (e.g., an endoscope, a duodenoscope, a ureteroscope, etc.). For example, a medical procedure may require accessing a target site via a tortuous path by bending or articulating one or more portions of the scope.

During an endoscopic procedure, for example, a user inserts a scope into a body lumen of a patient. The user utilizes actuation members on a handle of the endoscope to control the scope during insertion and/or during the procedure. A user may observe torque forces when operating the actuation members as the scope is bent using the actuation members. For example, as a user rotates an actuation member, such as a knob, from a neutral position, the user may observe a greater torque force as the actuation member is rotated further from the neutral position. This force may be related to an amount of material at bending regions on the scope. In some cases, reducing the material may reduce these forces. However, reduction of material may increase the difficulty of manufacturing the scope and/or may make the scope less robust. This disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes a handle, a shaft extending from the handle, first and second articulation wires coupled to the handle, and an articulation member at a distal end of the shaft. The articulation member includes a central longitudinal axis within a first bending plane, the first and second articulation wires lie within the first bending plane, the articulation member includes a plurality of links arranged about the central longitudinal axis, a first link of the plurality of links is attached to an adjacent, second link of the plurality of links via a first pair of hinges, a first hinge from the first pair of hinges is arranged on a first side the first bending plane, and a second hinge from the first pair of hinges is located on a second side of the bending plane, opposite the first side.

The first hinge and the second hinge each may include a body portion having a radially outer surface flush with a radially outer surface of each of the first link and the second link, and the first hinge and the second hinge each may include a protrusion extending from the body portion.

The protrusion may extend from an inner surface of the body portion toward the central longitudinal axis.

Each protrusion may define a slot receiving one of the first and second actuation wires, and the slot may be exposed to a lumen of the articulation member.

The exposed portion of the slot in the first hinge may face the first bending plane, and the exposed portion of the slot in the second hinge may face the first bending plane, and the slot in the first and second hinges may face opposite directions.

The protrusion may have a generally semi-circular shape in cross-section, and the slot may have a generally semi-circular shape in cross-section.

The device may further include a first articulation lumen extending through each of the plurality of links, and a second articulation lumen, parallel to the first articulation lumen, extending through each of the plurality of links, where the first articulation lumen may be in communication with the slot in the first hinge, and the second articulation lumen is in communication with the slot in the second hinge.

Proximal movement or distal movement of each of the first and second articulation wires may be configured to bend the articulation member.

Each of the first and second articulation wires may be configured to move within a corresponding slot to bend the articulation member.

The first and second articulation wires may lie in the bending plane when the articulation member is in a neutral position.

Bending the articulation member in a first direction relative to the first bending plane may cause the first articulation wire to be more exposed from a corresponding slot than the second articulation wire is exposed from a corresponding slot.

The device may further include a second pair of hinges connecting the second link to an adjacent, third link, the third link being different from the first link, and the second pair of hinges may be radially offset by ninety-degrees relative to the first pair of hinges.

The device may further include third and fourth articulation wires coupled to the handle and lying within a second bending plane containing the central longitudinal axis, where a first hinge from the second pair of hinges may be arranged on a first side of the second bending plane, and a second hinge from the second pair of hinges may be arranged on a second side of the second bending plane, opposite the first side.

Each of the pair of second hinges may include a protrusion defining a slot receiving an actuation wire, and the slot of each of the pair of second hinges may be exposed to a lumen of the articulation member.

The first bending plane may be orthogonal to the second bending plane.

According to another aspect, an articulation member for a medical device may include a first link, a second link, and a first hinge and a second hinge, the first hinge and the second hinge connecting the first link to the second link and arranged on radially opposite sides of the articulation member, where each of the first hinge and the second hinge includes a slot exposed to a central lumen of the articulation member, and where each slot is configured receive an articulation wire.

The articulation member may further include a third link adjacent the second link, and a third hinge and a fourth hinge connecting the third link to the second link, where the third hinge and the fourth hinge may be radially offset by ninety-degrees from the first hinge and the second hinge.

The first link and the second link ma define a first bending plane, where the third link and the fourth link may define a second bending plane, and where the second bending plane may be orthogonal to the first bending plane.

The first link may be positioned on a first side of the first bending plane and the second link may be positioned on a second side of the first bending plane, opposite the first side, and the third link may be positioned on a first side of the second bending plane and the fourth link may be positioned on a second side of the second bending plane, opposite the first side.

According to another aspect, a method for treating a patient includes advancing a distal end of a shaft to a target site in a patient, where the distal end includes an articulation member having a plurality of links, where adjacent links are connected via a pair of hinges, actuating a first actuator to bend the articulation member relative to a bending plane, where the bending plane includes a central longitudinal axis of the articulation member, and where a first link from the pair of links is positioned on a first side of the bending plane and a second link from the pair of links is positioned on a second side of the bending plane, opposite the first side, where bending the articulation member causes a first articulation wire to be exposed from the first hinge and a second articulation wire to be covered by the second hinge, and performing a medical procedure.

BRIEF DESCRIPTION OF THE DRAWINGS

The accompanying drawings, which are incorporated in and constitute a part of this application, illustrate various exemplary embodiments and together with the description, serve to explain the principles of exemplary embodiments.

DETAILED DESCRIPTION

Figure 1:
FIG. 1 is a schematic of a medical system according to one or more aspects of the disclosure.
Figure 1:
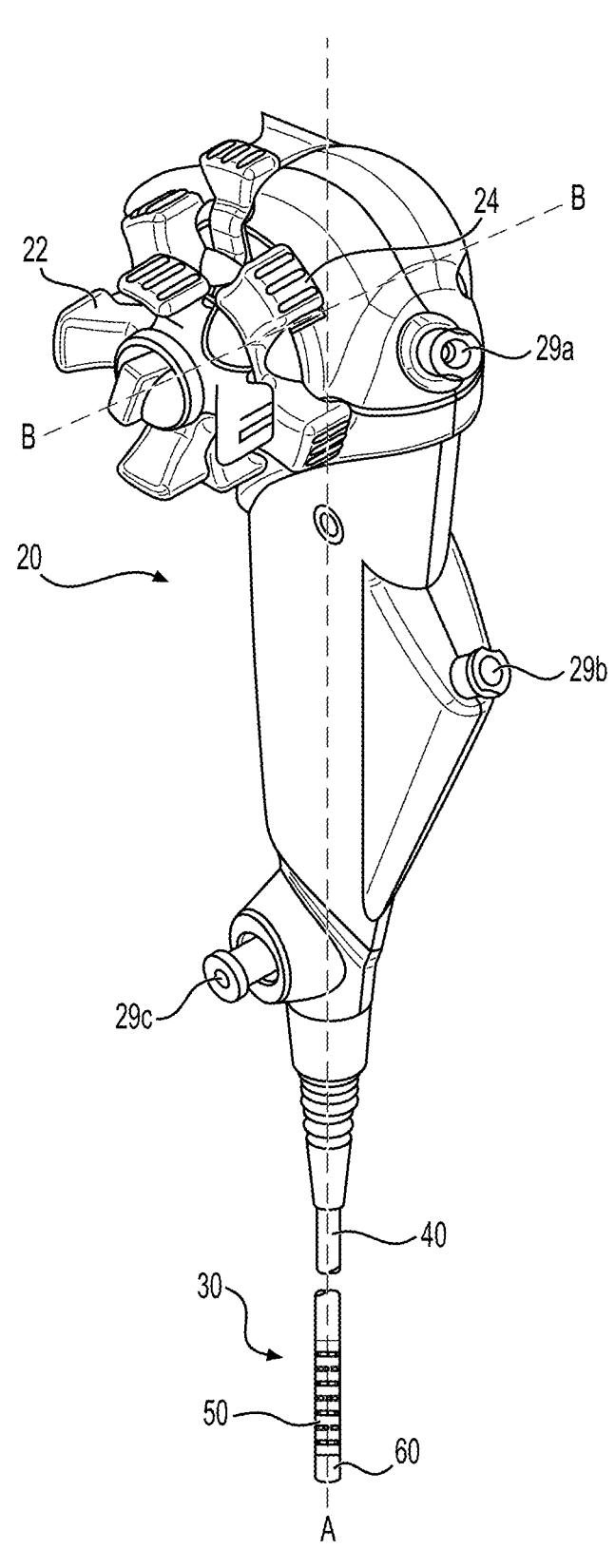

The disclosure is described with reference to exemplary medical systems for performing medical procedures using a scope (e.g., endoscope, ureteroscope, duodenoscope, colonoscope, or the like) on a target site. The devices associated with the medical systems may improve the functionality of the scope by reducing a force felt by an operator or a user, and/or may improve manufacturing of the scopes.

Reference to any particular device or procedure is provided in this disclosure only for convenience and not intended to limit the disclosure. A person of ordinary skill in the art would recognize that the concepts underlying the disclosed devices and methods may be utilized in any suitable device or procedure. For example, embodiments of the articulation member may be used in any medical device requiring a bending portion, including catheters, sheaths, scopes, and the like, and in any medical procedure, including laparoscopic, endoscopic, bronchoscopic, urologic, cardiovascular, and other procedures. The disclosure may be understood with reference to the following description and the appended drawings, wherein like elements are referred to with the same reference numerals.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

For ease of description, portions of the device and/or its components are referred to as proximal and distal portions. It should be noted that the term "proximal" is intended to refer to portions closer to a user of the device, and the term "distal" is used herein to refer to portions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/−10% of a stated or implied value. Additionally, terms that indicate the geometric shape of a component/surface include approximate shapes.

Referring to FIG. 1, a medical system 10 (also referred to herein as a medical device) according to some examples is shown. Medical system 10 includes a flexible shaft 30 (e.g., a catheter) and a handle 20 coupled to a proximal end of flexible shaft 30. Flexible shaft 30 may include a body 40 extending from handle 20, an articulation member 50 extending from a distal end of body 40, and a distal portion 60 extending from a distal end of articulation member 50. Body 40, articulation member 50, and distal portion 60 may be individual members connected together (e.g., via adhesive, rivets, screw threads, or any similar manner) or may be formed as a single, unitary member. Medical system 10 may include one or more lumens each extending through body 40, articulation member 50, and distal portion 60. Handle 20 may include multiple actuating devices (e.g., actuators) which control articulation of articulation member 50 in multiple directions, and movement of associated components and tools, as will be described herein. Handle 20, body 40, articulation member 50, and distal portion 60 extend along a central longitudinal axis A, which may define a neutral position of articulation member 50.

With continued reference to FIG. 1, handle 20 may include one or more ports 29a, 29b, 29c for inserting and/or removing tools, fluids, or other materials into and/or from the patient via shaft 30. Port 29b may be used to introduce one or more medical tools through a lumen (e.g., a working channel) of shaft 30. The medical tool may be any tool, such as, but not limited to, a snare, a knife, forceps, an ablation laser, or other suitable tool for performing a medical procedure. A distal opening (not shown) may be disposed in a distal end face of distal portion 60. The lumen, or a different lumen, may also be in communication with an umbilicus (not shown) via port 29a for introducing fluid and/or providing suction to the lumen. In addition, one or more electrical cables may extend from the proximal end of medical system 10 and/or the umbilicus to articulation member 50 and/or distal portion 60 and may provide a user with electrical control over imaging, lighting, and/or other electrical devices or components of medical system 10. Such electrical cables may carry imaging signals from the distal end of flexible shaft 30 proximally to be processed and/or displayed on a display. A third port 29*c* may provide access to one or more lumens described herein.

Figure 2A:
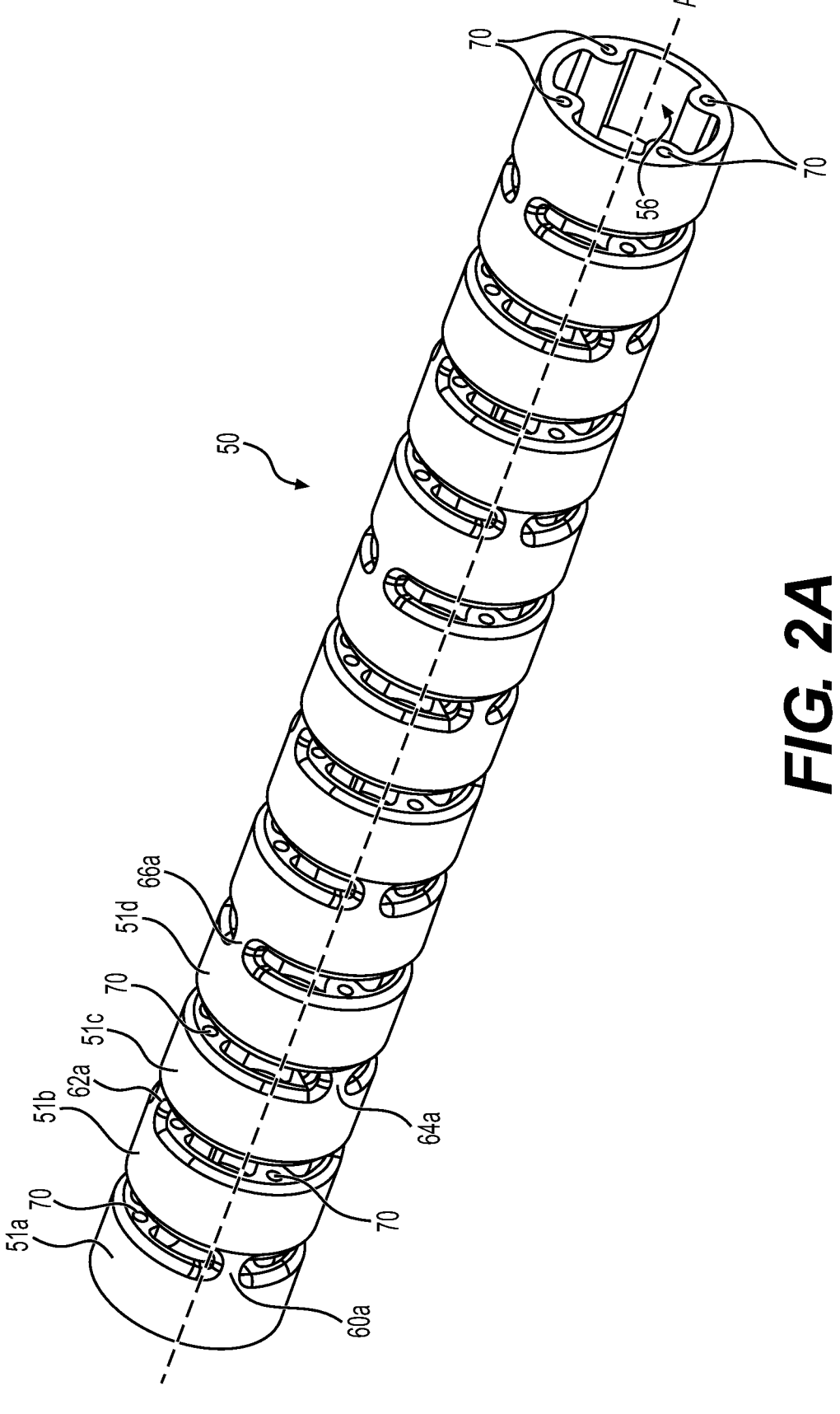
FIGS. 2A and 2B are perspective views of an articulation member of the medical system of FIG. 1.
Figure 2B:
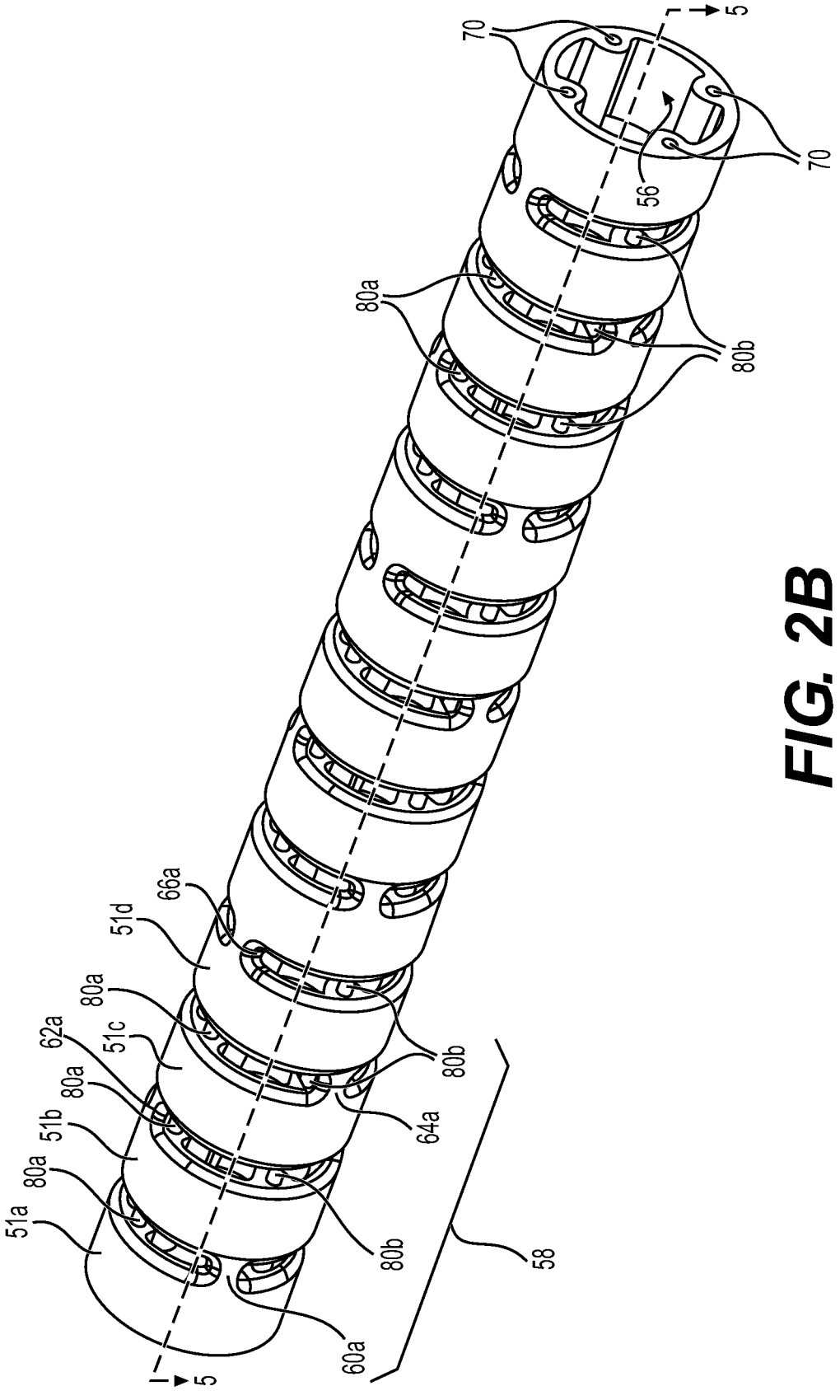

Articulation member 50 is shown in FIGS. 2A and 2B. Articulation member 50 may include a plurality of links 51, including a first link 51*a*, a second link 51*b*, a third link 51*c*, a fourth link 51*d*, etc. The number of links 51 is not limited. Adjacent links 51 may be connected via hinges or flexible regions. In some examples, hinges may be "living hinges" including a thin, flexible region formed as a unitary member with adjacent links 51 and including a material of articulation member 50. For example, first link 51*a* and second link 51*b* may be connected via a pair of first hinges 60*a*, 60*b*. First hinges 60*a*, 60*b* may be positioned on radial opposite sides of articulation member 50 from each other, for example 180 degrees from one another about axis A. Second link 51*b* and third link 51*c* may be connected by a pair of second hinges 62*a*, 62*b*. Second hinges 62*a*, 62*b* may be positioned on radial opposite sides of articulation member 50 from each other, for example 180 degrees from one another about axis A. Second hinges 62*a*, 62*b* may be radially offset by 90 degrees about axis A from first hinges 60*a*, 60*b*. Third link 51*c* and fourth link 51*d* may be connected by a pair of hinges 64*a*, 64*b*. Third hinges 64*a*, 64*b* may be positioned on radial opposite sides of articulation member 50 from each other, for example 180 degrees from one another about axis A.

The arrangement shown in the Figures may allow articulation member 50 to be deflected from a neutral position along longitudinal axis A in four directions, e.g., up, down, left, and right, each direction being approximately 90 degrees to an adjacent direction. Alternatively, it will be understood that the hinges may all be positioned along articulation member 50 such that articulation member may be deflected in only two directions, e.g., up and down or left and right. For example, articulation member 50 may include hinges that may allow articulation member 50 to bend in only two directions. In other words, articulation member 50 may be formed with hinges 60*a*, 60*b* and hinges 64*a*, 64*b*, but not hinges 62*a*, 62*b*. In this example, links 51*b*, 51*c* (and corresponding links 51 that allow articulation member 50 to bend in the same direction as links 51*b*, 51*c*) may be formed as a unitary member and/or may not move relative to each other.

Articulation member 50, including links 51 and hinges, may be formed as a single, unitary member, e.g., via extrusion molding or three-dimensional (3D) printing. Alternatively, adjacent links 51 of articulation member 50 may be attached via hinges using ultrasonic welding or the like. A material of articulation member 50 may include, for example, plastics that may be flexible at room temperature, such as nylon, polypropylene, polyethylene, polycarbonate, or the like. These materials may provide articulation member 50 sufficient flexibility to navigate a tortuous path while also providing sufficient rigidity to receive medical tools and to remove tissue when performing a medical procedure within the body.

With continued reference to FIGS. 2A and 2B, each link 51 includes four articulation wire lumens 70. Lumens 70 are equally spaced about each link 51, each lumen 70 being approximately 90 degrees about axis A from adjacent lumens 70. While four lumens 70 are shown, it will be understood that only two lumens 70, equally spaced about each link 51, may be provided. For example, four lumens 70 may allow articulation member 50 to be deflected from a neutral position along longitudinal axis A in four directions (up, down, left, and right), while two lumens 70 may allow articulation member 50 to be deflected in only two directions (up and down, or left, and right). Each link 51 may also include a generally central lumen such that a lumen 56 (e.g., FIGS. 4A and 4B) may be formed through articulation member 50 by the generally central lumen of each link 51. Lumen 56 may be fluidly connected to one or more corresponding lumens of body 40. Lumen 56 may receive one or more medical instruments (e.g., a grasper, a laser fiber, a suction device, scissors, a scalpel, etc.) such that a medical procedure may be performed on a target tissue, as described herein.

Figure 4A:
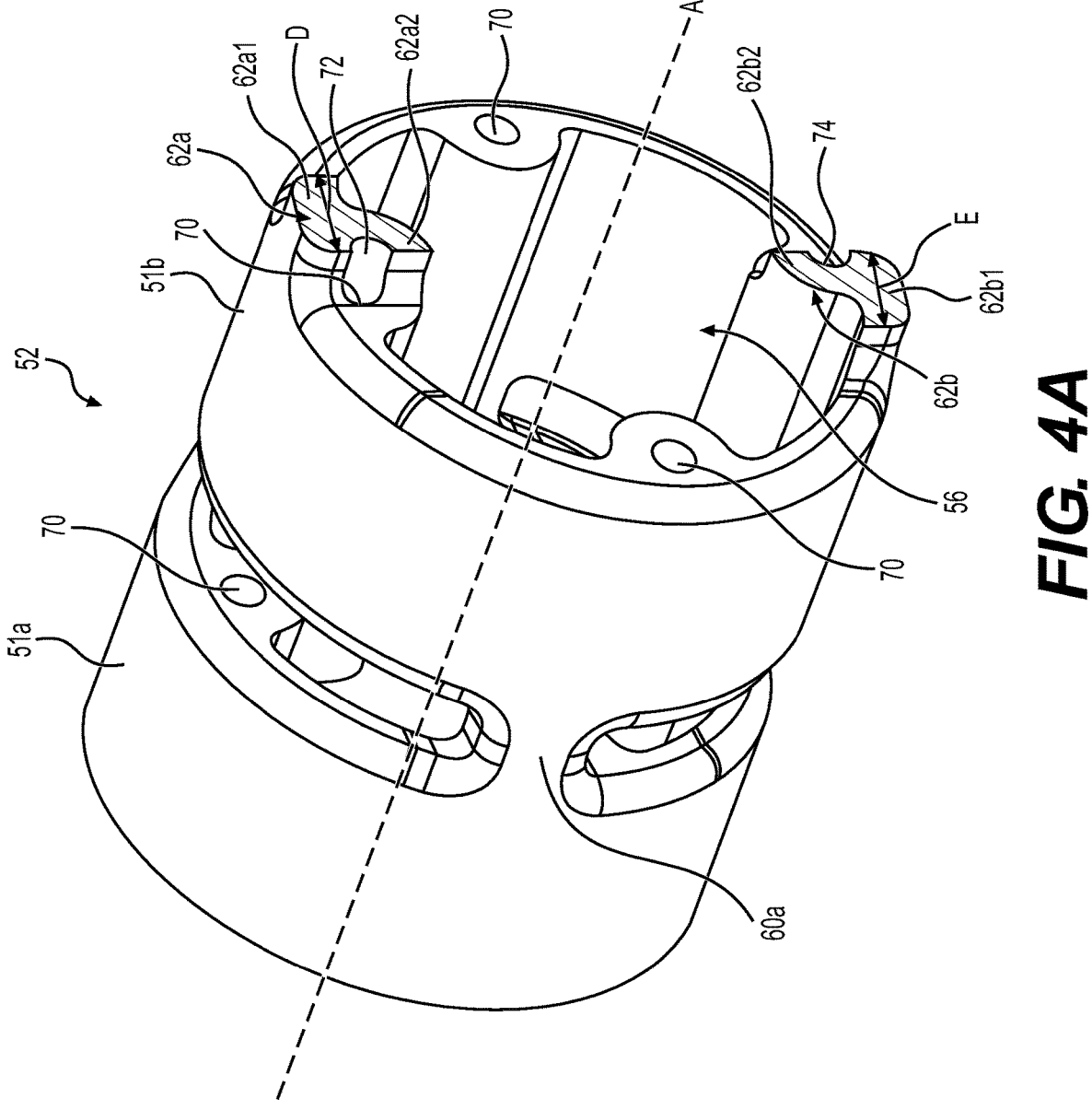
FIGS. 4A and 4B are perspective views of a segment of the articulation member of FIGS. 2A and 2B.
Figure 4B:
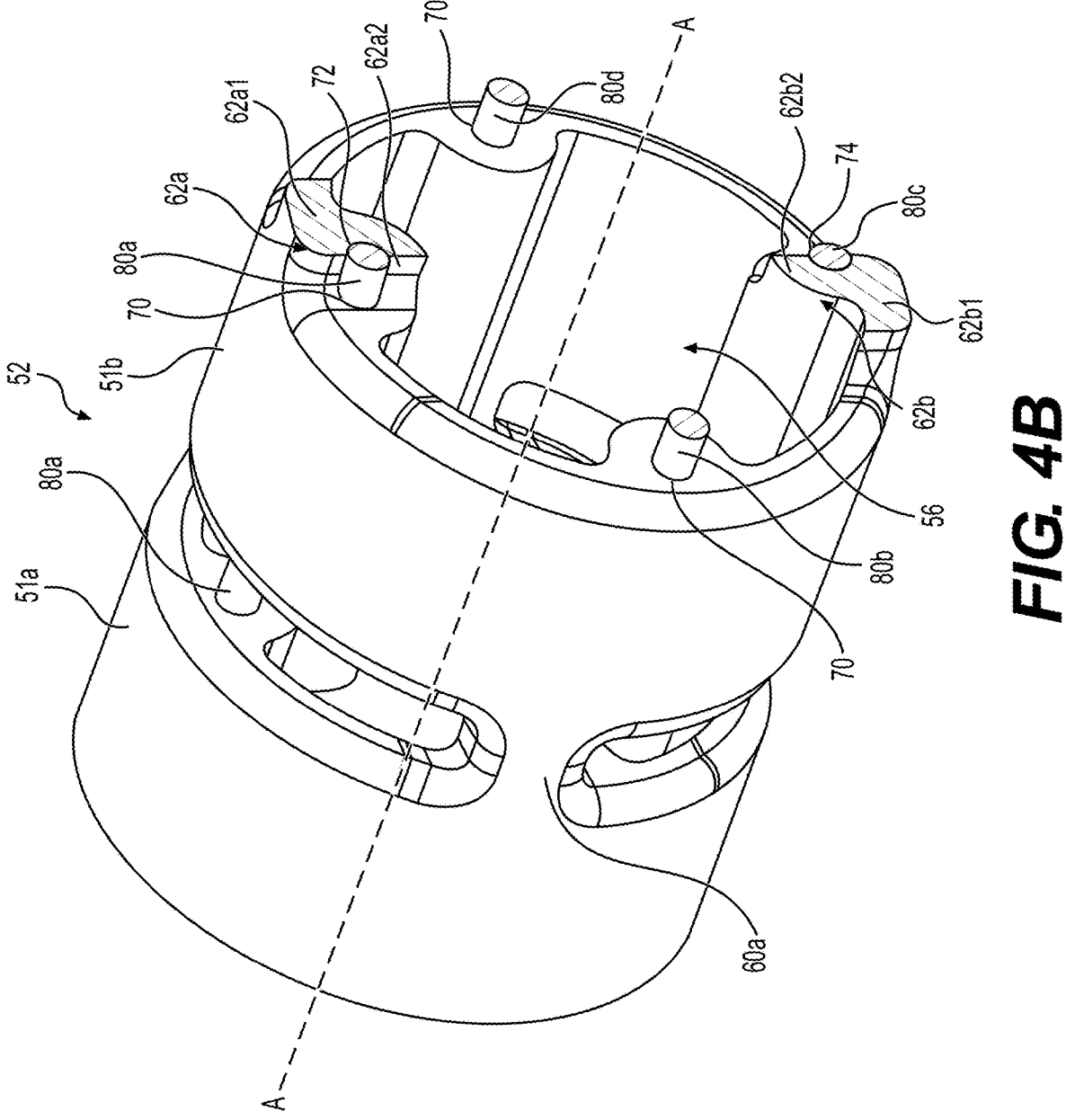

As shown in FIGS. 2B and 4B, articulation wires 80*a*, 80*b*, 80*c*, and 80*d* may be disposed in corresponding lumens 70. Each of articulation wires 80*a*, 80*b*, 80*c*, 80*d* may be connected at a distal end to distal portion 60 and/or a portion of articulation member 50 via adhesive, ultrasonic welding, crimping, or other similar technique. Proximal ends of articulation wires 80*a*, 80*b*, 80*c*, 80*d* may be connected to articulation control devices 22 or 24. For example, articulation wires 80*a*, 80*c* may be connected to control device 22. Rotational movement of control device 22 in a first direction, e.g., a clockwise direction, may cause articulation member 50 to bend in a first direction, e.g., up relative to longitudinal axis A. Rotating control device 22 in a second direction, e.g., a counterclockwise direction, may cause articulation member 50 to move in a second direction, e.g., down relative to longitudinal axis A. Articulation wires 80*b*, 80*d* may be attached to control device 24 and rotation of device 24 in a first direction and a second direction, e.g., a clockwise direction and a counterclockwise direction, may cause articulation member 50 to move relative to longitudinal axis A. For example, rotating control device 24 in the first direction may cause articulation member 50 to move right relative to longitudinal axis A. Rotating control device 24 in the second direction may cause articulation member 50 to move left relative to longitudinal axis A.

Figure 3A:
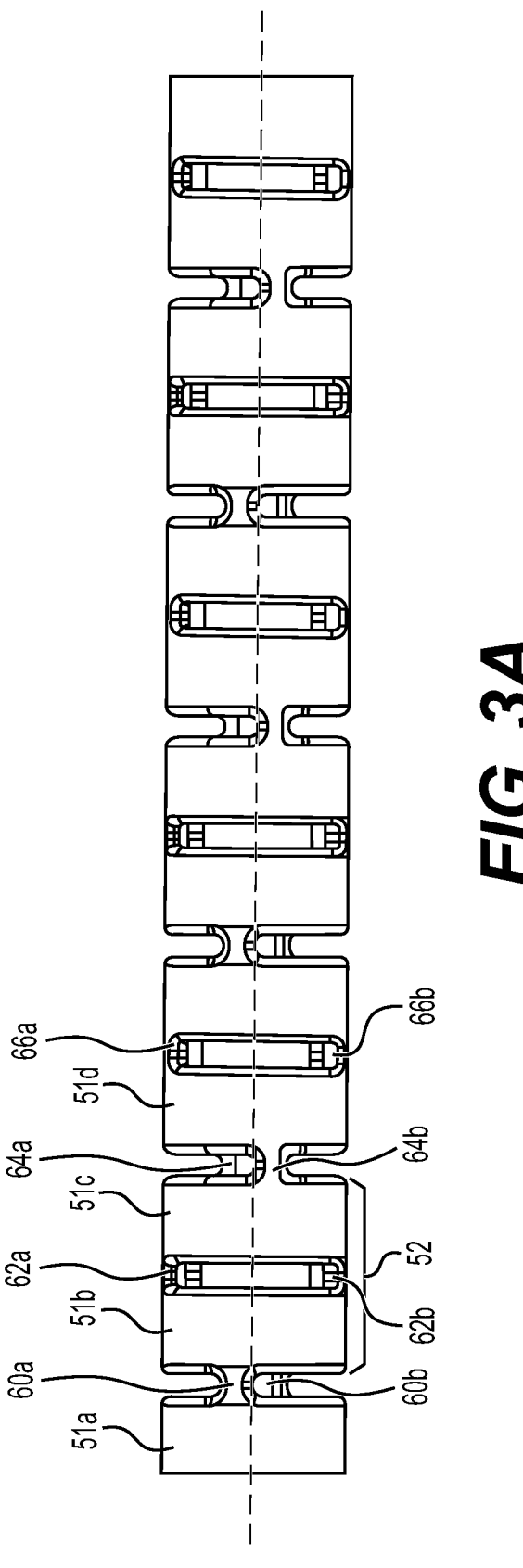
FIGS. 3A and 3B are side views of the articulation member of FIGS. 2A and 2B.
Figure 3B:
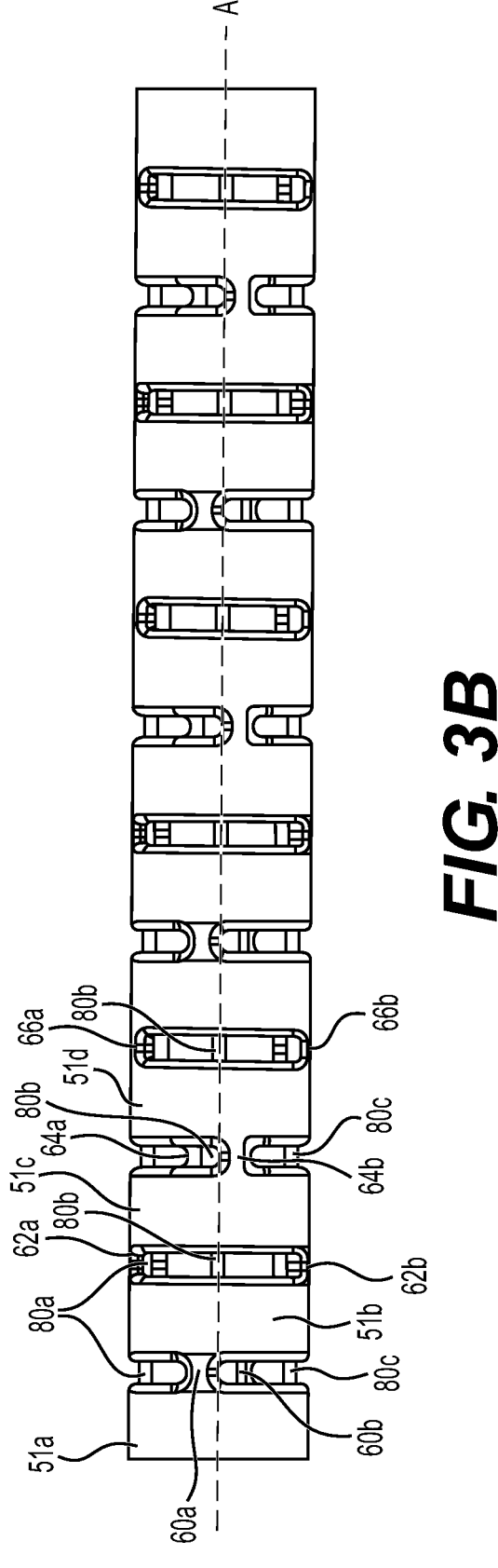

One or more bending planes may be defined by a plane perpendicular to the page of FIGS. 3A and 3B and along the longitudinal axis A shown in FIGS. 3A and 3B. Each hinge (e.g., hinge 60*a*, 60*b*, etc.) lies in a corresponding bending plane when articulation member 50 is in a straight configuration, as shown in FIG. 3B. FIG. 3A illustrates articulation member 50 as shown in FIG. 3B, but without articulation wires 80 for ease of understanding. Each of the bending planes may be offset by approximately five degrees in a clockwise direction and/or a counterclockwise direction for each successive set of hinges. This arrangement may cause articulation member 50 to bend along a bending plane located along longitudinal axis A, and actuation wires 80*b* and 80*d*, and their corresponding lumens 70, lie in that bending plane when articulation member 50 is in the straight configuration. The arrangement of offset bending planes may also cause articulation member 50 to twist in a helical shape as articulation member 50 bends from its proximal end to its distal end.

In addition, a bending segment is formed by, or includes, any two adjacent links 51, such as bending segment 52 that includes links 51*b*, 51*c*. Bending segment 52 may move relative to its adjacent link 51*a* via hinges 60*a*, 60*b*, and bending segment 52 may move relative to its adjacent link 51*d* via hinges 64*a*, 64*b*.

Hinge 60*a* may be positioned above the bending plane and longitudinal axis A and hinge 60*b* may be positioned below the bending plane and longitudinal axis A in FIG. 3A. The arrangement of hinges and wires allows a pivot point for bending segment 52 relative to link 51*a* to be located on or near the bending plane and longitudinal axis A. For example, as discussed above, actuating wire 80*b* extends parallel to longitudinal axis A as shown in FIG. 3B. Actuating wire 80*b* may allow bending segment 52 to bend relative to link 51*a* at a point along actuating wire 80*b*.

Hinge 64*a* may be positioned below the bending plane (e.g., a first bending plane) and longitudinal axis A, and hinge 64*b* may be positioned above the bending plane and longitudinal axis A. The arrangement of hinges and wires allows a pivot point for bending segment 52 relative to link 51*d* also to be located on or near the bending plane and longitudinal axis A. A second bending plane may be perpendicular to the first bending plane. For example, hinge 62*a* may be positioned above the second bending plane and hinge 62*b* may be positioned below the second bending plane (see. FIG. 2A). Similarly, hinge 66*a* may be positioned below the second bending plane and hinge 66*b* may be positioned above the second bending plane (FIG. 2B). This may allow articulation joint 50 to bend in directions perpendicular to the first bending plane (e.g., up and down as well as right and left). Links 51*a*, 51*b*, 51*c*, and 51*d*, and associated hinges 60, may form a bending unit 58 (FIGS. 2A, 2B, and 3A) which may enable articulation member 50 to bend in right, left, up, and down directions as described herein. Multiple bending units 58 may form articulation member 50. For example, articulation member 50 may include any number of bending units 58 connected in series or, alternatively, formed as a unitary member in series, based on a desired and/or necessary length of articulation member 50. This arrangement of hinge locations above or below the bending plane may be selected by the user such that a bias or a twist in bending of articulation member 50 alternates between links to balance each other and deflect in a flat plane or to compound with each other and form a helix, based on an anatomy of the patient and/or a path for accessing a target site.

FIGS. 4A and 4B show links 51*a* and 51*b* and cross-sections of adjacent hinges 62*a* and 62*b*. Some or all of the hinges throughout member 50 may have the same or similar structure as hinges 62*a* and 62*b*, which will now be described.

Hinge 62*a* may include a body portion 62*a*1 extending generally parallel to longitudinal axis A between link 51*b* and link 51*c*. A radially outer surface of body portion 62*a*1 may be flush with a radially outer surface of articulation member 50. Body portion 62*a*1 has a width that is measured perpendicular to axis A and in line with body portion 62*a*2, a height that is measured perpendicular to axis A and perpendicular to the width of body portion 62*a*1, and a length that is measured parallel to axis A. The width of body portion 62*a*1 may be approximately 0.020 inches to approximately 0.150 inches. For example, a length of the width of body portion 62*a*1 may be sufficient for body portion 62*a*1 to encompass a diameter of an articulation wire and to include two walls of sufficient thickness on either side of the articulation wire. The length of body portion 62*a*1 may be approximately 0.020 inches to approximately 0.200 inches and may depend on the flexibility of the material and the desired bend angle of hinge 62*a* in each direction. Hinges (e.g., hinge 62*a*) may include a material capable of flexing at operating temperatures and may include one or more of nylon, polypropylene, polyethylene, or polycarbonate, or any composite thereof. The material may provide a sufficient balance of flexibility to articulation member 50 during bending and may provide sufficient resistance to compression or torsion in operation, as well as rigidity/structural integrity during manufacturing of articulation member 50. A material and/or a size of hinge 62*a* may be any material suitable to allow hinge 62*a* to bend or flex. A protrusion 62*a*2 may extend generally perpendicular from body portion 62*a*1 toward longitudinal axis A. Protrusion 62*a*2 may define a generally semi-circular slot 72, which may extend parallel to longitudinal axis A. Additionally, slot 72 may be open to lumen 56 of articulation member 50 (e.g., FIGS. 4A and 4B). It will be understood that slot 72 may be rectangular, or any other suitable shape, in cross-section. A shape of a cross-section of protrusion 62*a*2 may be similar to that of slot 72, e.g., the shape may be semi-circular. Semi-circular slot 72 may be an extension of a corresponding lumen 70 in links connected by hinge 62*a*, e.g., link 51*b* and adjacent link 51*c* (not shown in FIGS. 4A and 4B). Slot 72 may receive articulation wire 80*a* such that a portion of articulation wire 80*a* may be exposed from slot 72, as shown in FIG. 4B. Wire 80*a* is therefore exposed to lumen 56 that extends through member 50.

Hinge 62*b* may have a similar design as hinge 62*a*. For example, a body portion 62*b*2 may extend generally parallel to longitudinal axis A. Body portion 62*b*1 and body portion 62*b*2 may have dimensions similar to those of body portions 62*a*1 and 62*a*2 based on a desired articulation of articulation member 50 in a direction perpendicular to hinges 60*a*, 60*b*, which may provide sufficient rigidity to articulation member 50 during bending and/or during manufacturing of articulation member 50. Each of a width, a height, and a length of body portions 62*b*1 or 62*b*2 may be the same and/or may be different from the width, the length, and the height, respectively, of body portions 62*a*1 or 62*a*2. If width, height, and length of each body portion are different dimensions, a user may feel a different amount of torque when articulating articulation member 50 in different directions. A protrusion 62*b*2 may extend generally perpendicular from body portion 62*b*2 toward longitudinal axis A. A generally semi-circular slot 74 may be formed in protrusion 62*b*2 and may extend parallel to longitudinal axis A. Additionally, slot 74 may be open to lumen 56 of articulation member 50 (e.g., FIGS. 4A and 4B). As with slot 72, the cross-sectional shape of slot 74 is not limited. A shape cross-section of protrusion 62*b*2 may be similar to that of slot 74, e.g., the shape may be semi-circular. Slot 74 may receive wire 80*c* such that a portion of wire 80*c* is exposed, as shown in FIG. 4B. The reduced size of protrusions 62*a*2 and 62*b*2, relative to sizes of conventional hinges, may reduce an amount of material of hinges 62*a* and 62*b*. This may reduce the force necessary to bend articulation member 50 at hinges 62*a* and 62*b*, which may reduce an amount of torque necessary to be applied at control devices 22 and/or 24. In this manner, the force necessary to bend articulation member 50 may be reduced, which may reduce fatigue and/or pain by a user. While not shown, all hinges, e.g., hinges 60*a*, 60*b*, may be similar in cross-section to hinges 62*a*, 62*b*. For example, the slots in each hinge may face different directions, but may all be open to lumen 56 of articulation member 50.

Figure 5:
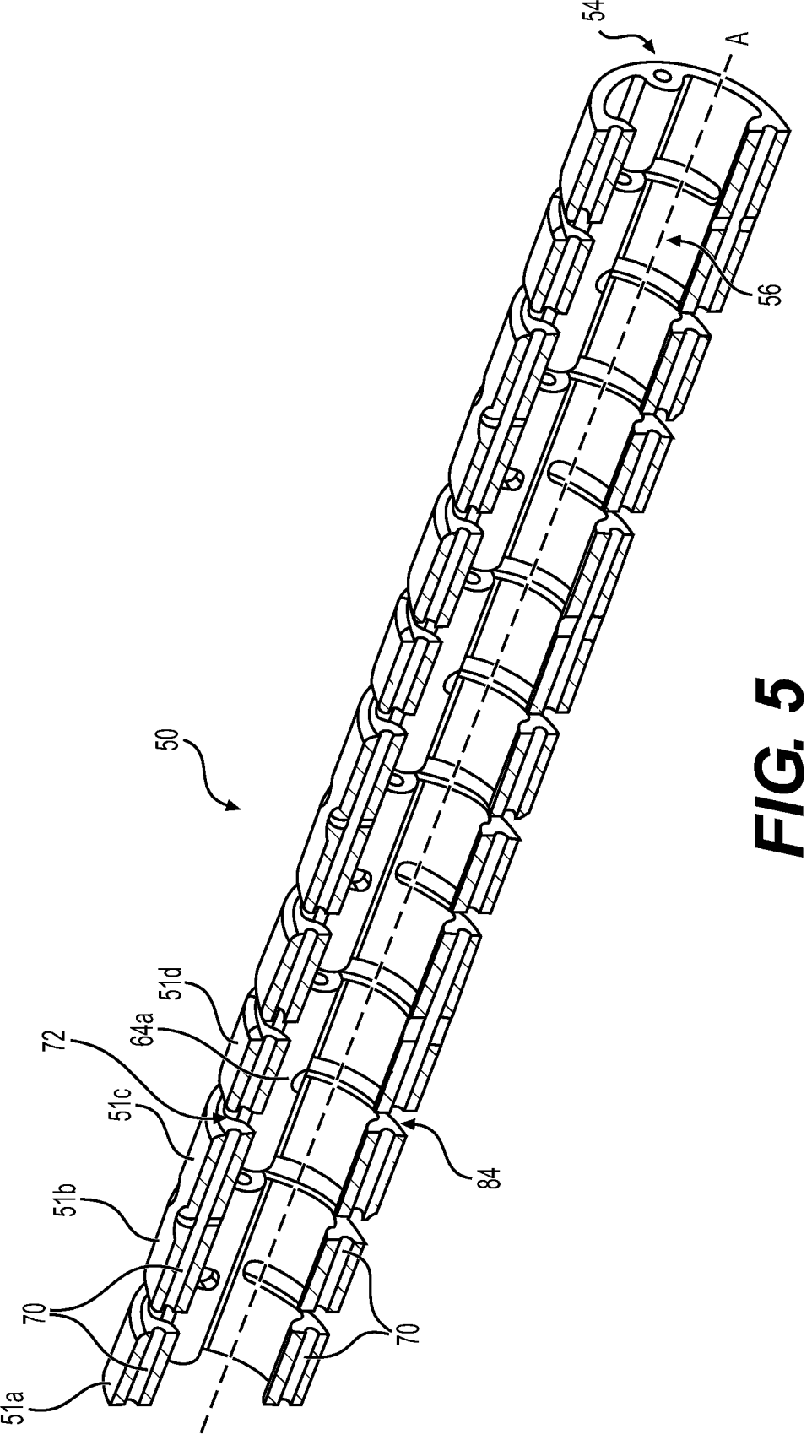
FIG. 5 is a cross-section of the articulation member taken along the line 5-5 in FIG. 2B.

A cross-section of articulation member 50 taken along line 5-5 in FIG. 2B is shown in FIG. 5. The cross-section illustrates body portion 62*a*1 of hinge 62*a* and body portion 62*b*1 of hinge 62*b*, which connect links 51*b* and 51*c*. Gaps 82 and 84 are between links 51*c* and 51*d*. Gaps 82 and 84 are in regions between links 51*c* and 51*d* that are not filled by hinges 64*a*, 64*b* which connect links 51*c* and 51*d*. Each gaps 82, 84 may be rectangular in cross-section and have a partial annular shape. Two gaps, e.g., gap 82 and gap 84, may be formed between adjacent links 51, e.g., links 51*c* and 51*d*, in the regions not filled by hinges. Alternatively, gaps 82, 84 may be V-shaped, U-shaped, or Y-shaped. Gaps 82, 84 may be variable across a length of articulation member 50 which may elicit specific bending behavior and/or may allow procedural access to a target site. For example, changing a size and/or a position of the gaps may change a bend radius and/or an amount of articulation of articulation member 50 in the up/down and/or the left/right directions.

Figure 6:
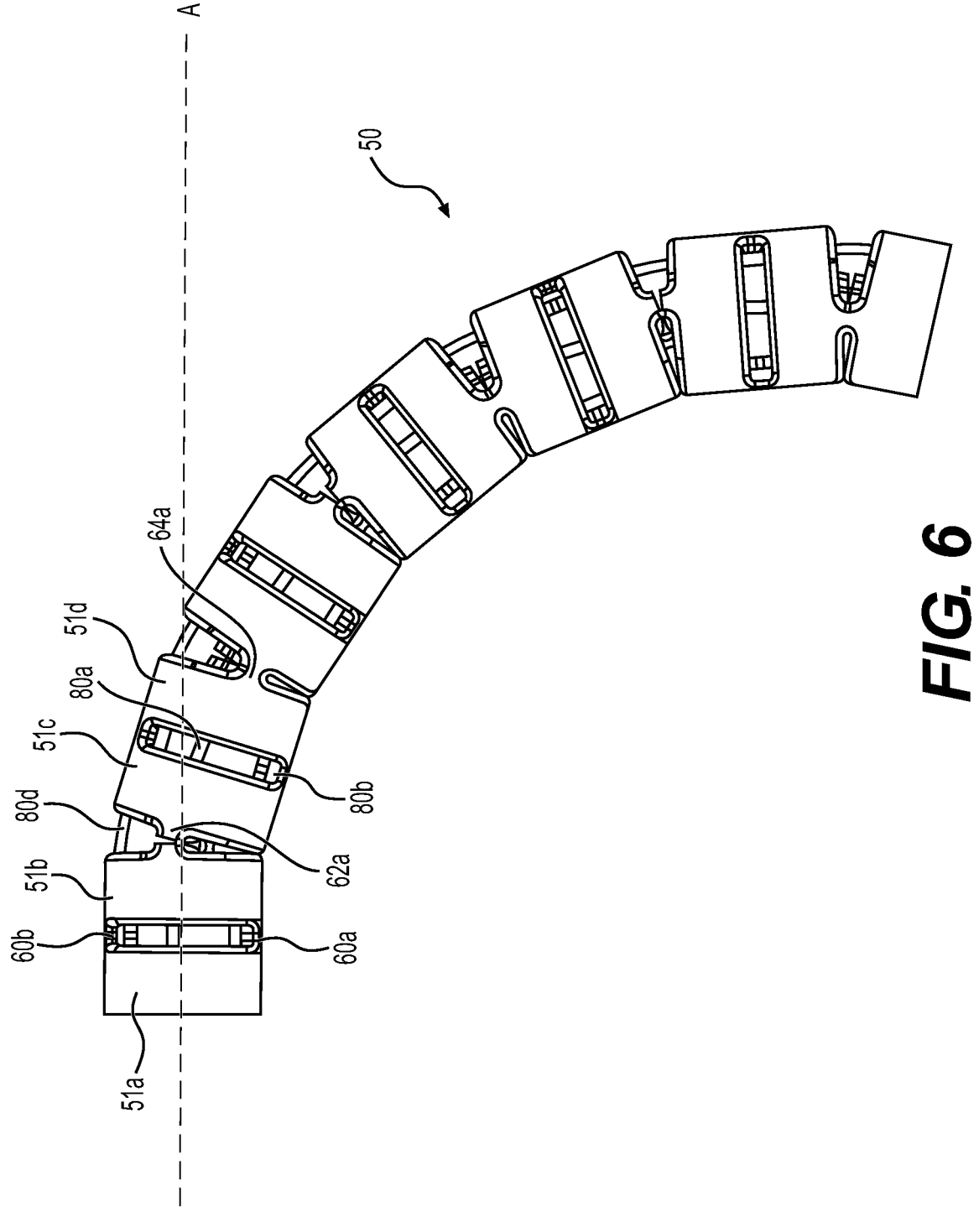
FIG. 6 is a side view of the articulation member of FIGS. 2A and 2B in a bent configuration.

Cross-sections of articulation wire lumens 70 are also shown in FIG. 5. Articulation wire lumens 70 extend parallel to longitudinal axis A. Articulation wire lumens 70 may be circular in cross-section, or may have any other suitable cross-sectional shape. A distal end of each of articulation wires 80*a*, 80*b*, 80*c*, 80*d* may be attached at a distal end 54 of articulation member 50 using crimping, adhesive, welding, or other suitable fastening mechanism. Alternatively, or additionally, distal end portion 60 (which may include imaging, lighting, and other structural features, including an end effector) may be attached to distal end 54. In another example, articulation wires 80*a*, 80*b*, 80*c*, 80*d* may be attached to distal end portion 60. Actuation of control devices 22 and/or 24 may cause articulation wires 80*a*, 80*b*, 80*c*, 80*d* to move proximally and distally within corresponding lumens 70 of links 51 and slots between lumens 70. Proximal movement of one or more of articulation wires 80*a*, 80*b*, 80*c*, 80*d* may cause articulation member 50 to bend from a first position, generally parallel to longitudinal axis A, to a second position, in which articulation member 50 is angled relative to longitudinal axis A, as shown in FIG. 6. Distal movement of one or more of articulation wires 80*a*, 80*b*, 80*c*, 80*d* may cause articulation member 50 to bend from the second position shown in FIG. 6 to the first position.

A method of performing a medical procedure using medical system 10 will be described. Distal end 54 of articulation member 50 (and distal end portion 60) may be inserted into the body via an opening (a natural orifice or an incision in the patient). Alternatively, distal end 54 of articulation member 50 may be advanced to the target site via an access catheter previously positioned within the body.

Once distal end 54 of articulation member 50 (and distal end portion 60) is positioned at the target site, articulation member 50 may be actuated. Alternatively, or additionally, articulation member 50 may be actuated as the distal end 54 is advanced to the target site to, for example, navigate tortuous paths. To actuate articulation member 50, one or both of control members 22, 24 may be actuated. For example, a user may rotate control member 22, which may cause actuation member 50 to move in an up-down direction. Similarly, rotation of control member 24 may cause actuation member 50 to move in a left-right direction. As a user rotates one or both of control members 22, 24, a force felt by the user may be less than a force when using conventional articulation members. For example, as control members 22, 24 are rotated and articulation member 50 is bent relative to longitudinal axis A (e.g., FIG. 6), the reduced material of hinges 62, 64, 66, etc., may reduce a force necessary to bend articulation member 50.

Furthermore, slots 72, 74 may alternately expose and/or hide articulation wires 80 as articulation member 50 is bent relative to longitudinal axis A. For example, as articulation member 50 bends in a first direction, hinge 62*a* may bend to further expose slot 72 and, thus, further expose articulation wire 80*a*. This bending movement may also cause hinge 62*b* to bend to close off slot 74, which may hide or prevent articulation wire 80*c* from being seen (FIG. 6). As articulation member 50 is bent in the opposite direction, slot 72 may close, while further exposing slot 74. Similar movement in a direction orthogonal to hinges 62*a*, 62*b* may expose or hide slots in hinges 64. As articulation member bends in a second direction, opposite the first direction, hinge 62*a* may bend to close of slot 72 and, thus, hide slot 74.

It will be understood that one or more instruments or tools may be advanced along lumen 56 to perform a medical procedure at the target site. The user may continue to actuate control members 22, 24 to provide access to the target site from different directions, which may aid in performing the medical procedure. Additionally, or alternatively, tissue and/or fluids may be removed from the target site using suction, graspers, or the like. Once the medical procedure is complete, articulation member 50 may be removed from the body.

It will be understood that articulation member 50 may include any number of links 51. Further, the hinges connecting the links 51 may be positioned around articulation member 50 in any manner.

Medical system 10 may allow a user to operate a catheter, scope, sheath, or other device having an articulation member using less force than conventional articulation members. In this manner, the user may be able to perform a medical procedure in a more timely and/or cost effective manner, while minimizing harm to a patient. Moreover, medical system 10 may have fewer manufacturing failures, which may result in reduced costs for medical system 10 and/or the medical procedures using the same.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
a handle;
a shaft extending from the handle;
first and second articulation wires coupled to the handle; and
an articulation member at a distal end of the shaft, wherein the articulation member includes a central longitudinal axis within a first bending plane;
a first articulation lumen; and
a second articulation lumen, parallel to the first articulation lumen,
wherein the first and second articulation wires lie within the first bending plane, wherein the articulation member includes a plurality of links arranged about the central longitudinal axis,
wherein each of the first articulation lumen and the second articulation lumen extends through each of the plurality of links,
wherein each of the first articulation lumen and the second articulation lumen has a circular cross-sectional shape,
wherein a first link of the plurality of links is attached to an adjacent, second link of the plurality of links via a first pair of hinges,
wherein a first hinge from the first pair of hinges is arranged on a first side of the first bending plane, wherein the first hinge includes a first protrusion extending toward the central longitudinal axis, and wherein the first protrusion includes a first slot having a partially circular cross-sectional shape, wherein the first articulation lumen is in communication with the first slot, and wherein a second hinge from the first pair of hinges is located on a second side of the first bending plane that is opposite the first side of the first bending plane, wherein the second hinge includes a second protrusion extending toward the central longitudinal axis, and wherein the second protrusion includes a second slot having a partially circular cross-sectional shape and the second articulation lumen is in communication with the second slot.

2. The medical device of claim 1, wherein the first hinge and the second hinge each includes a body portion having a radially outer surface flush with a radially outer surface of each of the first link of the plurality of links and the second link of the plurality of links, and wherein the first protrusion extends from the body portion of the first hinge and the second protrusion extends from the body portion of the second hinge.

3. The medical device of claim 1, wherein the first slot receives the first articulation wire and, wherein the second slot receives the second articulation wire, and wherein each of the first slot and the second slot is exposed to a lumen of the articulation member.

4. The medical device of claim 1, wherein an exposed portion of the first slot faces the first bending plane, and wherein an exposed portion of the second slot faces the first bending plane, and the exposed portion of the first slot and the exposed portion of the second slot face opposite directions.

5. The medical device of claim 1, wherein each of the first protrusion and the second protrusion has a semi-circular shape in cross-section, and wherein each of the first slot and the second slot has a semi-circular shape in cross-section.

6. The medical device of claim 1, wherein proximal movement or distal movement of each of the first and second articulation wires is configured to bend the articulation member.

7. The medical device of claim 6, wherein the first articulation wire is configured to move within the first slot and the second articulation wire is configured to move within the second slot to bend the articulation member.

8. The medical device of claim 6, wherein the first and second articulation wires lie in the first bending plane when the articulation member is in a neutral position.

9. The medical device of claim 1, wherein bending the articulation member in a first direction relative to the first bending plane causes the first articulation wire to be more exposed from the first slot than the second articulation wire is exposed from the second slot.

10. The medical device of claim 1, further comprising a second pair of hinges connecting the second link of the plurality of links to an adjacent, third link of the plurality of links, and wherein the second pair of hinges are radially offset by ninety-degrees relative to the first pair of hinges.

11. The medical device of claim 10, further comprising third and fourth articulation wires coupled to the handle and lying within a second bending plane containing the central longitudinal axis, wherein a first hinge from the second pair of hinges is arranged on a first side of the second bending plane, and wherein a second hinge from the second pair of hinges is arranged on a second side of the second bending plane, opposite the first side of the second bending plane.

12. The medical device of claim 10, wherein each of the second pair of hinges includes a protrusion defining a slot receiving an actuation wire, and wherein the slot of each of the pair of second hinges is exposed to a lumen of the articulation member.

13. The medical device of claim 10, wherein the first bending plane is orthogonal to the second bending plane.

14. An articulation member for a medical device, the articulation member comprising:
    a first link having a first lumen and a second lumen, wherein the first lumen has a circular cross-sectional shape and the second lumen has a circular cross-sectional shape;
    a second link having a third lumen and a fourth lumen, wherein the third lumen has a circular cross-sectional shape and the fourth lumen has a circular cross-sectional shape; and
    a first hinge and a second hinge, the first hinge and the second hinge connecting the first link to the second link and arranged on radially opposite sides of the articulation member,
    wherein the first hinge includes a first slot having a partially circular cross-sectional shape, and the second hinge includes a second slot having a partially circular cross-sectional shape,
    wherein each of the first slot and the second slot is exposed to a central lumen of the articulation member,
    wherein the first slot is disposed between the first lumen and the third lumen,
    wherein the second slot is disposed between the second lumen and the fourth lumen,
    wherein the first slot, the first lumen, and the third lumen are configured to receive a first articulation wire, and
    wherein the second slot, the second lumen, and the fourth lumen are configured to receive a second articulation wire.

15. The medical device of claim 14, wherein each of the first slot and the second slot has a semi-circular cross-sectional shape.

16. A method for treating a patient, the method comprising:
    advancing a distal end of a shaft to a target site in a patient, wherein the distal end of the shaft includes an articulation member having a plurality of links, wherein adjacent links are connected via a first hinge and a second hinge;
    actuating a first actuator to bend the articulation member relative to a bending plane, wherein the bending plane includes a central longitudinal axis of the articulation member, and wherein the first hinge is positioned on a first side of the bending plane and the second hinge is positioned on a second side of the bending plane, opposite the first side of the bending plane,
    wherein a first articulation wire extends through a first lumen of each of the plurality of links, wherein the first lumen of each of the plurality of links has a circular cross-sectional shape, wherein a second articulation wire extends through a second lumen of each of the plurality of links, wherein the second lumen of each of the plurality of links has a circular cross-sectional shape,
    wherein the first hinge includes a first slot connecting the first lumen of each of the adjacent links, wherein the first slot has a partially circular cross-sectional shape, wherein the second hinge includes a second slot connecting the second lumen of each of the adjacent links, wherein the second slot having a partially circular cross-sectional shape,
    wherein bending the articulation member causes the first articulation wire to be exposed from the first slot of the first hinge to a central lumen extending through the plurality of links and the second articulation wire to be covered by the second hinge closing off the second slot; and performing a medical procedure.

* * * * *